ations of Tortuous Vessels.
United States Patent [19]
Yoshimura et al.

[11] 4,345,602
[45] Aug. 24, 1982

[54] MEDICAL VASCULAR GUIDE WIRE AND SELF-GUILDING TYPE CATHETER

[75] Inventors: Hidenaga Yoshimura, Tokyo; Kunio Yamada, Nishio; Hironori Yamada, Okazaki; Ryusaku Yamada, Osaka; Hiroaki Kudo, Nara, all of Japan

[73] Assignees: Toray Monofilament Company Limited, Aichi; Osaka City Government, Osaka, both of Japan

[21] Appl. No.: 116,600

[22] Filed: Jan. 29, 1980

[30] Foreign Application Priority Data

Feb. 8, 1979 [JP] Japan .................................. 54-12814
Oct. 26, 1979 [JP] Japan .................................. 54-137558
Oct. 26, 1979 [JP] Japan .................................. 54-137559
Oct. 26, 1979 [JP] Japan .................................. 54-137560
Oct. 26, 1979 [JP] Japan .................................. 54-137561

[51] Int. Cl.³ ........................................ A61M 25/00
[52] U.S. Cl. ............................... 128/349 R; 128/348; 128/DIG. 9
[58] Field of Search ............. 128/349 R, 348, DIG. 9, 128/DIG. 16, 350 R

[56] References Cited
U.S. PATENT DOCUMENTS 2,688,329 9/1954 Wallace ..................... 128/DIG. 9 X
3,435,826 4/1969 Fogarty ............................... 128/348
3,500,820 3/1970 Almen .......................... 128/348 X
3,687,142 8/1972 Leibinzohn .............. 128/DIG. 9 X

FOREIGN PATENT DOCUMENTS 131266 6/1975 Denmark ...................... 128/DIG. 9

OTHER PUBLICATIONS

Br. J. Radiol, 42, pp. 227-229 (1969), Cornell et al., A Refinement in Catheter Angiography of Abdominal Aortic Aneurysms, The J-Tip Movable Core Guide Wire.
"Radiology", 88, (II), pp. 1127-1130 (1969), Judkins et al., Lumen-Following Safety J-Guide for Catheterization of Tortuous Vessels.
"Am. J. Roentgenol, Red, Therapy & Nuclear Med.," 97, (2), pp. 508-510 (1966), Nebesar et al., A Curved-Tip Guide Wire.
"Am. J. Roentgenol, Red, Therapy & Nuclear Med.," 97, (2), pp. 511-518 (1966), Rossi et al., The Floppy Wire, Aid in Catheterization.
"JAMA," vol. 229, No. 7, pp. 817-818 (1974), Blitt et al., Central Venous Catheterization Via The External Jugular Vein, A Technique Employing the J-Wire.

Primary Examiner—Paul J. Hirsch
Assistant Examiner—Mickey Yu
Attorney, Agent, or Firm—Austin R. Miller

[57] ABSTRACT

Disclosed is a medical vascular guide wire made of a synthetic resin hollow monofilament. The guide wire is comprised of a tip part, a flexible part having a smaller diameter than the other parts, a tapering part and a manipulating part, these four parts continuously forming in line, in that order, along the monofilament axis. At least the tip part and the manipulating part have X-ray impermeable material inserted in the respective hollows thereof. A self-guiding type catheter made of a synthetic resin, multi-hollow monofilament is also provided. The catheter is comprised of a tip part, a flexible part having a smaller diameter than the other parts, a tapering part and a manipulating part, these four parts continuously formed in line, in that order, along the monofilament axis: The catheter has at least two hollows extending at least from one end of the manipulating part to the tapering part or to the other end of the manipulating part or to a point in close proximity to said other end of the manipulating part. At least one of the hollows has an X-ray impermeable material inserted at least within the hollow in the manipulating part, and the other hollow or at least one of the other hollows form a lumen for permitting a liquid and/or a gas to pass therethrough.

16 Claims, 12 Drawing Figures

MEDICAL VASCULAR GUIDE WIRE AND SELF-GUILDING TYPE CATHETER

BACKGROUND OF THE INVENTION

1. Field of the Invention

This invention relates to a medical vascular guide wire for aiding the insertion of a catheter into, particularly, blood vessels of the living body for withdrawal of blood and other specimens from the affected parts, or for infusion of a drug solution to the affected parts. It also relates to a self-guiding type catheter, namely, a catheter capable of guiding its tip to the peripheral blood vessels in the affected parts.

2. Description of the Prior Art

Most conventional guide wires are coil-form metal wires supplied by, for example, COOK Inc., Universal Medical Instrument Corp. and USCI, a division of C. R. Bard, Inc. These coiled metal wires have some disadvantages. Namely, first, the coiled metal wires possess an uneven surface, and hence, thrombi are liable to be deposited thereon. Secondly, the metal wires are too rigid to permit their tips to reach the blood vessels in the affected parts without causing undue strain or pain to the patient, or taking a great deal of time. Thirdly, the coiled metal wires are not easy to manipulate so that their tips will reach the affected parts. Fourthly, there is a danger that the coiled metal wires may injure the intimae of blood vessels.

Most conventional catheters are made of synthetic resin tubes and supplied by, for example, Universal Medical Instrument Corp., Electro-Catheter Corp. and USCI, a division of C. R. Bard, Inc. These catheters are used in combination with the aforesaid metal guide wires. These catheters also have some disadvantages. That is first, the catheters are larger in diameter than the guide wires, and, therefore, it is difficult for the catheter tip to reach the intended location, particularly in peripheral blood vessels, where the guide wire has reached. Furthermore, it is generally difficult to accomplish the catheterization without causing undue strain or pain to the patient. Secondly, in the process of catheterization, many kinds of catheters and guide wires must be used in combination. Thus, the procedure requires a substantially long period of time.

SUMMARY OF THE INVENTION

Therefore, an object of the present invention is to provide a medical vascular guide wire, which has a smooth surface on which thrombi are deposited only to a slight extent, which is sufficiently flexible for permitting it to reach peripheral blood vessels in the affected parts without undue strain to the patient or taking a great deal of time, which is capable of being easily manipulated and which does not injure the intimae of blood vessels.

Another object of the present invention is to provide a self-guiding type catheter, namely, a catheter capable of guiding its tip to the peripheral blood vessels, which catheter possesses advantageous characteristics similar to those mentioned above in the object directed to the guide wire.

Other objects and advantages of the present invention will be apparent from the following description.

In one aspect of the present invention, there is provided a medical vascular guide wire comprising a wire body made of a synthetic resin hollow monofilament and comprised of a tip part, a relatively flexible part having a smaller diameter than the other parts, a tapering part and a manipulating part, these four parts continuously forming in line, in that order, along the monofilament axis, and; at least the tip part and the manipulating part having X-ray impermeable material inserted in the respective hollows thereof.

In another aspect of the present invention, there is provided a self-guiding type catheter comprising a continuously extending body made of a synthetic resin multi-hollow monofilament and comprised of a tip part, a relatively flexible part having a smaller diameter than the other parts, a tapering part and a manipulating part, these four parts continuously formed in line, in that order, along the monofilament axis;

said body having at least two hollows extending at least from one end of the manipulating part to the tapering part or to the other end of the manipulating part or to a point in close proximity to said other end of the manipulating part, at least one of said hollows having an X-ray impermeable material inserted at least within the hollow in the manipulating part, and the other hollow or at least one of the other hollows forming a lumen for permitting a liquid and/or a gas to pass therethrough, which lumen is opened to the outside of the body through an inlet opening at the distal end of the lumen and through an outlet opening bored in the tapering part or in the adjacent portion thereto of the manipulating part and;

said body further having at least two hollows in the tip part, at least one of said hollows having an X-ray impermeable material inserted therein.

DESCRIPTION OF THE PREFERRED EMBODIMENTS

Figure 1A:
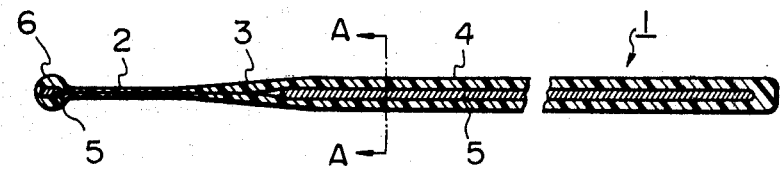
FIG. 1A is an enlarged longitudinal sectional view illustrating one example of the guide wire of the invention.
Figure 1B:
FIG. 1B is an enlarged transverse sectional view taken along the line A—A in FIG. 1.

Referring to FIGS. 1A and 1B, the guide wire 1 is comprised of a tip part 6, a relatively flexible part 2 (which is hereinafter referred to as "flexible part" for brevity), a tapering part 3 and a manipulating part 4. These four parts continuously form in line, in that order, along the monofilament axis. The tip part 6 is of a hollow structure and has X-ray impermeable material 5 inserted therein. The shape of the tip part 6 is not particularly limited but may preferably be spherical, oval spherical or end-rounded cylindrical. The size of the tip part 6 is preferably about 0.5–3 mm, more preferably about 0.7–2 mm, in maximum diameter, and preferably about 0.5–5 mm, more preferably about 0.7–4 mm, in length.

The flexible part 2 may be either hollow or solid and possesses a substantially uniform diameter over its entire length. The size of the flexible part 2 is preferably about 0.1–0.5 mm, more preferably about 0.15–0.4 mm, in diameter, and preferably about 10–100 mm, more preferably about 20–70 mm, in length. The flexible part 2 possesses a smaller diameter, and is more flexible and pliable than the other parts, and furthermore, is sufficiently strong to prevent the guide wire from being broken between the tip part 6 and the flexible part 2.

The tapering part 3 tapers from its end adjacent to the manipulating part 4 toward the flexible part 2. The size of the tapering part 3 is preferably about 10–100 mm, more preferably about 20–70 mm, in length. Although there may be no clear demarcation between the tapering part 3 and the flexible part 2, the total length of these two parts should preferably be not larger than 200 mm. The tapering part 3 may be either hollow or solid. It is, however, preferable that the tapering part 3 be hollow and have X-ray impermeable material inserted therein.

The manipulating part 4 is of a hollow monofilament structure. Its diameter is preferably about 0.5–3 mm, more preferably about 0.7–2 mm. Its length should be at least about 200 mm, preferably 50–200 cm and more preferably 70–150 cm. The manipulating part 4 has X-ray impermeable material 5 in the form of a wire of about 0.2–0.4 mm in diameter, inserted in the hollow thereof. The manipulating part 4 should preferably possess a high toughness and suitable degree of rigidity.

The above-mentioned numerical values for the size of the guide wire are mere exemplifications and it should be understood that the size of the guide wire is not particularly limited to such values.

The respective parts of the guide wire of the invention have the following functions. The tip part 6 is capable of freely moving in blood vessels and does not intrude into the walls of blood vessels. That is, the tip part 6 floats in the blood stream and reaches the intended parts without even a slight strain being caused on the patient, and therefore, there is no risk of injuring the intimae of blood vessels. This is in a striking contrast to conventional metal guide wires, which must be forced into blood vessels. The flexible part 2 permits the free movement of the tip part 6 in blood vessels. The tapering part 3 between the flexible part 2 and the manipulating part 4, ensures the unrestricted manipulation of the guide wire. Namely, a highly skilled and delicate manipulation of the guide wire can be easily effected, which manipulation is required for advancing the guide wire into the intended blood vessel branch at a turning point. Furthermore, the synthetic resin monofilament has a smooth surface and therefore, thrombi are deposited thereon only to a slight extent.

The guide wire of the invention may be made of any melt-extrudable thermoplastic synthetic resins. The thermoplastic synthetic resins used include, for example, polyesters, such as polyethylene terephthalate and polybutylene terephthalate; polyamides, such as nylon-6, nylon-66, nylon-610, nylon-11, nylon-12 and nylon-6/66; polyolefins, such as polyethylene and polypropylene; and, fluorine-containing resins, such as copolymer of tetrafluoroethylene with hexafluoropropylene. These thermoplastic synthetic resins may be used either alone or in combination.

The most preferable thermoplastic synthetic resins are a polyblend comprised of, based on the total weight of the polyblend, (i) 70 to 99% by weight of at least one melt-extrudable thermoplastic synthetic resin selected from the above-mentioned polyesters, polyamides and polyolefins, and (ii) 1 to 30% by weight of a fluorine-containing thermoplastic resin, such as polytetrafluoroethylene and polyvinylidene fluoride. The optimum amount of the fluorine-containing thermoplastic resin in the polyblend is from 3 to 15% by weight. The guide wire made of the above-mentioned polyblend exhibits an enhanced self-lubricating property. Therefore, the undesirable deposition of thrombi can be substantially avoided and, in addition, the manipulation of the guide wire is very easy. The guide wire made only of a melt-extrudable fluorine-containing thermoplastic synthetic resin also exhibits an enhanced self-lubricating property.

The X-ray impermeable (or radio-opaque) material is inserted at least in the tip part and the manipulating part of the guide wire, so that the guide wire can be monitored from the outside of the patient body during the introduction of the guide wire into blood vessels. The X-ray impermeable material used includes, for example metal wires, such as a tungsten wire, and liquid contrast media, such as "CONRAY" (trade name, 60 w/v% methylglucamine iothalamate, supplied by, Mallinkrodt Inc.) and "UROGRAFIN" (trade name, methylglucamine and sodium diatrigoate, supplied by Schering A. G.). These X-ray impermeable materials may be used either alone or in combination. Of these, tungsten is preferable because of its high radio-opacity.

The X-ray impermeable material to be inserted in the hollow of the tip part 6 may be of any shape or form, such as a finely divided powder, a rod and a sphere. Its size may be, for example, about 0.2 mm in diameter for the spherical or powdered material, and about 0.2 mm in diameter and about 0.4–0.6 mm in length for the rod-shaped material. The X-ray impermeable material to be inserted in the hollow of the manipulating part 4 may preferably be continuously extending wire, such as a tungsten wire, for imparting proper toughness and rigidity to the manipulating part. This metal wire is usually inserted over the entire length of the manipulating part, and its diameter is preferably about 0.2–0.4 mm.

Figure 6:
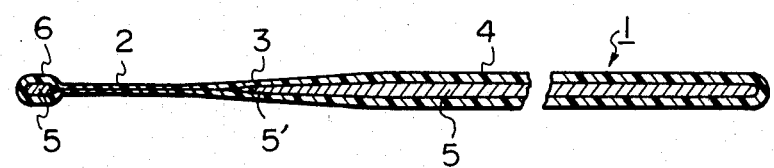
FIG. 6 is an enlarged longitudinal sectional view illustrating another example of the guide wire of the invention.

The medical vascular guide wire illustrated in FIG. 6 is similar to that of FIGS. 1A and 1B, but with an X-ray impermeable metal wire 5, one end portion 5' of which is tapered toward the flexible part 2. The metal wire 5 is inserted in the hollow of the tip part 6 and the hollow extending from one end of the manipulating part 4 to a midway point of the tapering part 3. The tapered metal wire 5 exhibits an enhanced flexibility, as compared with the non-tapered metal wire illustrated in FIG. 1A, and thus, the guide wire can be more unrestrictedly moved in blood vessels and more easily manipulated.

The hollow monofilament body of the guide wire of the invention can be surface-treated in order to enhance its self-lubricating property and, thus, to completely avoid the risk of thrombus deposition and to make the manipulation of the guide wire easy. The surface treatment employed includes (i) a silicone treatment, (ii) a fluorine-containing resin coating treatment or (iii) a plasma spark discharge treatment. These surface treatments can be effected as follows.

(i) Silicon coating treatment

A hollow monofilament body is passed several times through a bath of a solution of a medical silicone disolved in, for example, isopropanol, and then, the so coated monofilament body is dried under reduced pressure, thereby removing the solvent therefrom. Prior to the silicone coating treatment, the monofilament body may be surface-treated with sandpaper in order to facilitate the silicone coating treatment.

(ii) Fluorine-containing resin coating treatment

A hollow monofilament body is treated with a solution of a fluorine-containing resin, such as "Teflon 30 J" (trade name, an aqueous suspension containing about 60 weight % of finely divided polytetrafluoroethylene having a particle size of about 0.3 micron, supplied by Mitsui Fluorochemical Co.) and "Teflon D-1" (trade name, an aqueous suspension of finely divided polytetrafluoroethylene, supplied by Daikin Kogyo K.K.). The treating procedure may be similar to that explained above with regard to the silicone coating treatment.

(iii) Plasma spark discharge treatment

A hollow monofilament body is placed in a chamber which is maintained at a reduced pressure of below about 1 mmHg and into which a small amount of a gaseous organic fluorocompound is introduced. Then, a plasma spark discharge is effected, thereby introducing fluorine substituents into the polymer forming the surface of the monofilament.

The medical vascular guide wire of the invention may be manufactured as follows. A thermoplastic synthetic resin is melt-extruded through an annular orifice of a spinneret provided in an extruder, to obtain an undrawn or slightly drawn continuous hollow monofilament. The continuous hollow monofilament is cut into predetermined lengths. A portion of the entire length of each hollow monofilament, which portion is adjacent to one end portion thereof, is drawn several times its original length, whereby a relatively flexible part and a tapering part are simultaneously formed. X-ray impermeable material is inserted into the hollow of the undrawn or slightly drawn end portion thereof and, then, its open end is heat-sealed to form the tip part. X-ray impermeable material is also inserted into the continuously extending hollow of the manipulating part from the end thereof opposite to the tip part and, then, the open end is heat-sealed. When the guide wire illustrated in FIG. 6 is manufactured, an X-ray impermeable metal wire, one end portion of which is tapered, is inserted so that the tapered end reaches a midway point of the tapering part.

The guide wire of the invention can be inserted into peripheral blood vessels so that its tip part is advanced to the affected parts, by a conventional manipulation procedure. Then, a catheter may be inserted in the blood vessels so that the catheter advances along the inserted guide wire.

The self-guiding type catheter will now be illustrated with reference to FIGS. 7A through 8B.

Figure 7A:
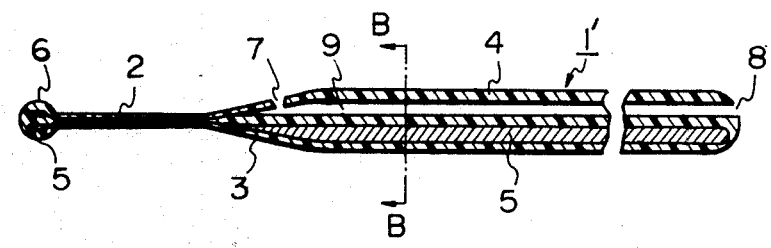
FIG. 7A is an enlarged longitudinal sectional view illustrating one example of the self-guiding type catheter of the invention.
Figure 7B:
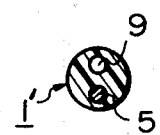
FIG. 7B is an enlarged cross-sectional view taken along the line B—B in FIG. 7A.

Referring to FIGS. 7A and 7B, the self-guiding type catheter 1' is made of a multi-hollow monofilament body having two continuously extending hollows and comprised of a tip part 6, a relatively flexible part 2, a tapering part 3 and a manipulating part 4. X-ray impermeable material 5 is inserted in one of the continuously extending hollows at least in the tip part 6 and in the manipulating part 4, and both ends of the X-ray impermeable material inserted hollow are closed. The other continuously extending hollow 9 forms a lumen for permitting liquid and/or gas, such as a drug solution, to pass therethrough, which lumen is opened to the outside of the monofilament body through an inlet opening 8 at one end of the lumen 9 and through an outlet opening 7 bored in the tapering part 3. The outlet opening 7 may be bored not in the tapering part 3 but in a portion of the manipulating part 4, adjacent to the tapering part 3. The structure and function of the tip part 6, the flexible part 2 and the tapering part 3 are similar to those of the guide wire explained with reference to FIGS. 1A and 6. The outlet opening 7 bored in the tapering part 3 or in a portion, adjacent thereto, of the manipulating part 4 preferably has a sectional shape, shown in FIG. 7A, such that the section becomes broader toward the outside of the monofilament body so as to avoid the undesirable retentivity of a drug solution. The inlet opening 8 may be capped when the catheter is not used. Furthermore, the end portion of the monofilament body, having the inlet opening 8, may preferably be of a structure such that a connector or an injector can be connected thereto.

The self-guiding type catheter having the structure mentioned above with reference to FIGS. 7A and 7B is characterized as being very pliable and easy to manipulate. Thus, it is easy to manipulate the catheter, inserted by degrees in blood vessels, so that the tip part of the catheter reaches the intended parts through large diameter curved blood vessels and small peripheral blood vessels. A drug solution may be introduced into the catheter through the inlet opening thereof after the tip part thereof reaches the intended parts and, as a result, the drug solution can be selectively administered to the intended parts. Thus, a medical treatment can be accomplished without taking a great deal of time, i.e., without repeated insertion and withdrawal of guide wires and catheters. In stead of the infusion of a drug solution, the self-guiding type catheter may be used for, for example, the withdrawal of blood and other specimens and the monitoring of heart functions.

Figure 7C:
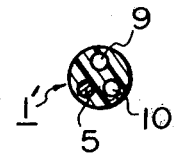
FIG. 7C is an enlarged cross-sectional view illustrating a self-guiding type catheter similar to that illustrated in FIGS. 7A and 7B, but with three hollows.

It is preferable that the multi-hollow monofilament body of the catheter have an exactly circular cross-section, at least over the entire length of the manipulating part, in order to make the insertion of the catheter into blood vessels and the manipulation thereof easy, and furthermore, to minimize the leakage of blood. In this regard, the multi-hollow monofilament body should preferably have at least three continuously extending hollows, instead of two continuously extending hollows as illustrated in FIGS. 7A and 7B. It is easy to prepare a multi-hollow monofilament possessing an exactly circular cross-section in the case where the monofilament has three continuously extending hollows as illustrated in FIG. 7C, one hollow has X-ray impermeable material 5 inserted therein and another hollow forms a lumen 9 for infusion of a drug solution. The remaining hollow 10 is closed, i.e., heat-sealed, at both ends. Alternatively, this remaining hollow 10 may have X-ray impermeable material inserted therein or form a lumen for infusion of a drug solution. It is also possible to provide four or more continuously extending hollows in the multi-hollow monofilament body.

Figure 8A:
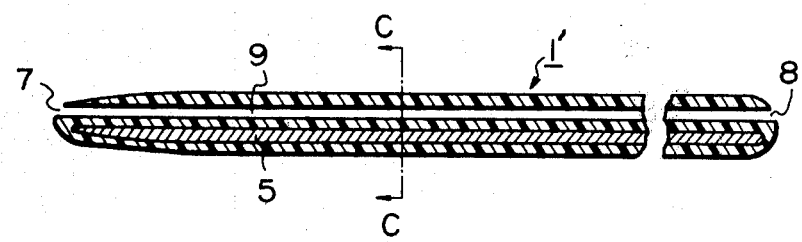
FIG. 8A is an enlarged longitudinal sectional view illustrating another example of the self-guiding type catheter of the invention; and, FIG. 8B is an enlarged transverse section view taken along the line C—C in FIG. 8A.
Figure 8B:
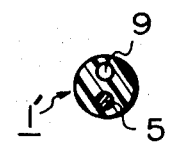

One modification of the self-guiding type catheter of FIGS. 7A and 7B, is illustrated in FIGS. 8A and 8B.

The catheter 1' illustrated in FIGS. 8A and 8B is composed of a multi-hollow monofilament body having a substantially uniform diameter over the entire length thereof and two continuously extending hollows, one of the hollows having X-ray impermeable material inserted therein and the other forming a lumen 9 for infusion of a drug solution. This type catheter is poor in flexibility as compared with the catheter illustrated in FIGS. 7A and 7B, and therefore, may be used in the case where the affected parts can be reached only through blood vessels having a large diameter and having no tortuous portions.

The thermoplastic synthetic resin used for the preparation of the multi-hollow monofilament body of the catheter and the X-ray impermeable material to be inserted in the hollow of the monofilament body may be similar to those mentioned hereinbefore with regard to the guide wire.

The size of the multi-lumene monofilament body of the catheter of the invention may also be similar to that of the guide wire mentioned hereinbefore, but is preferably somewhat larger than the guide wire. More specifically, the tip part preferably has a maximum diameter of about 0.5–3 mm, more preferably about 0.7–2 mm, and a length of about 0.5–5 mm, more preferably 0.7–4 mm. The flexible part preferably has a diameter of about 0.1–0.5 mm, more preferably about 0.15–0.4 mm, and a length of about 10–100 mm, more preferably about 20–70 mm. The tapering part preferably has a length of about 10–100 mm, more preferably about 20–70 mm. The manipulating part preferably has a diameter of about 0.5–3 mm, more preferably 0.7–2 mm, and a length of at least about 20 cm, more preferably about 50–200 cm. These sizes may be suitably varied depending upon, for example, the age and the physical condition of the patient or the state of the parts for which a treatment is intended. It is preferable that the continuously extending hollows in the monofilament body have a large diameter.

The self-guiding type catheter of the invention may be manufactured as follows. A thermoplastic synthetic resin is melt-extruded through an annular orifice of a multi-hollow type spinneret equipped in an extruder to obtain an undrawn or slightly drawn continuous multi-hollow monofilament. The multi-hollow monofilament is cut into predetermined lengths. A portion of the entire length of each multi-hollow monofilament, which portion is adjacent to one end portion thereof, is drawn several times its original length, whereby a flexible part and a tapering part are simultaneously formed. X-ray impermeable material is inserted into at least one of the hollows in the undrawn or slightly drawn end portion of the monofilament, and then, its open end is heat-sealed to form the tip part. X-ray impermeable material is also inserted into the hollow of the manipulating part from the end thereof opposite to the tip part, and then, the open end is heat-sealed. In the case where a tungsten wire is used as the X-ray impermeable material, it is preferable that one end portion of the tungsten wire be tapered and inserted in the hollow of the manipulating part so that its tapered tip end is directed to the tip part of the catheter. Then, an outlet opening 7 (refer to FIG. 7A) is drilled through the wall of the tapering part by using a fine drill. The end portion of the monofilament body, which has an inlet opening 8 (FIG. 7A), may be provided with a cap or an adaptor to connect the catheter with an infusion pump. The multi-hollow monofilament body of the catheter may be surface-treated in manners similar to those hereinbefore described with regard to the guide wire. Such a surface treatment enhances the self-lubricating property of the catheter, and thus, enables the minimization of thrombus deposition and makes the manipulation very easy.

The invention will now be illustrated by the following examples.

EXAMPLE 1

Polyethylene terephthalate was melt-extruded in a conventional manner, by using an extruder provided with a spinneret having an annular orifice to obtain an undrawn hollow monofilament having an overall diameter of 0.7 mm and a hollow diameter of 0.35 mm. A tungsten piece of wire, 0.25 mm in diameter and 0.6 mm in length, was inserted in one end portion of the hollow monofilament, which portion had a length of 0.7 mm. Then, the open end was heat-sealed to form a tip part of a guide wire. Thereafter, the portion adjacent to the tip part was drawn to form a flexible part 0.3 mm in diameter and 3 cm in length and a tapering part 0.3–0.7 mm in diameter and 4 cm in length. A tungsten wire having a diameter of 0.3 mm was inserted into a manipulating part 0.7 mm in diameter and 1,500 mm in length, and then, its open end was heat-sealed to thereby obtain a monofilament guide wire.

The clinical applications of the monofilament guide wire to blood vessels were indicated as follows.

Figure 2:
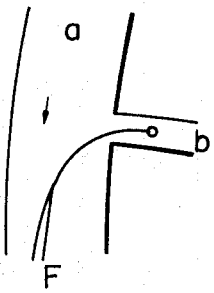
FIGS. 2 through 5 are diagrammatical views illustrating the state of the guide wire inserted in various blood vessels.

(i) The tip part of the guide wire (F) was advanced through the abdominal aorta (a) into the left renal artery (b) (refer to FIG. 2).

Figure 3:
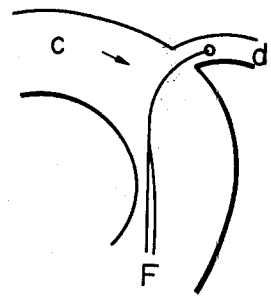

(ii) The tip part of the guide wire (F) was advanced through the aortic arch (c) into the carotid artery (d) (refer to FIG. 3).

Figure 4:
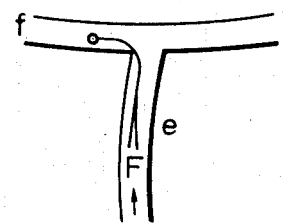

(iii) The tip part of the guide wire (F) was advanced from the abdominal aorta through the coeliac artery (e) into the hepatic artery (f) (refer to FIG. 4).

Figure 5:
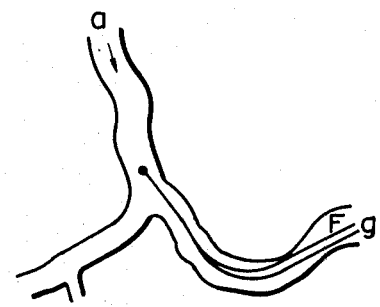

(iv) The tip part of the guide wire (F) was advanced through the femoral artery (g) into the abdominal aorta (a) (refer to FIG. 5).

In FIGS. 2 through 5, an arrow indicates the direction in which blood flows and "F" indicates the guide wire. In all cases of (i) through (iv), listed above, the guide wire could be easily manipulated and it did not injure the walls of blood vessels. On the contrary, conventional coiled metal guide wire was difficult to advance into the intended peripheral blood vessel branches.

EXAMPLE 2

Polyethylene terephthalate was melt-extruded in a conventional manner by using an extruder provided with a spinneret having an annular orifice to obtain a hollow monofilament having an overall diameter of 0.8 mm and a hollow diameter of 0.33 mm. The monofilament was cut into lengths of 1.3 m. A portion of each monofilament, which portion was adjacent to one end portion of the monofilament, was drawn about three times its original length to simultaneously form a flexible part 0.3 mm in diameter and 20 mm in length and a tapering part 30 cm in length. Then, a tungsten piece having a diameter of 0.3 mm and a length of 1.5 mm was inserted in the undrawn end portion, and then, its open end was heat-sealed, to thereby form an oval spherical tip part 0.8 mm in diameter and 2.5 mm in length. Thereafter, a tungsten wire having a tapered end portion and having a diameter of 0.25 mm and a length of 1.25 m was inserted in the other undrawn portion from the open end thereof, so that the tapered tip of the tungsten wire reached a midway point of the tapering part, and then, the open end was heat-sealed, whereby a synthetic resin monofilament guide wire was obtained.

The adaptation of the guide wire to the blood vessel contour was tested by carrying out procedures similar those listed in Example 1. Even when the tip part of the guide wire was advanced into the carotid artery (d) making an acute angle with the aortic arch (c) (refer to FIG. 3) or advanced through the tortuous femoral artery (g) into the abdominal aorta (a) (refer to FIG. 5), the guide wire could be easily manipulated without injury to the patient.

EXAMPLE 3

A hollow monofilament having an overall diameter of 0.8 mm and a hollow diameter of 0.33 mm was prepared, in a manner similar to that mentioned in Example 2, from a molten mixture comprised of 95 weight % of polyethylene terephthalate and 5 weight % of a polytetrafuoroethylene resin "TLP-10" (trade name, supplied by Mitsui Fluorochemical Co.). The monofilament was cut into lengths of 1.3 m. A portion of each monofilament, which portion was adjacent to one end portion of the monofilament, was drawn about three times its original length to simultaneously form a flexible part 0.3 mm in diameter and 50 mm in length and a tapering part 30 mm in length. Then, a tungsten piece 0.3 mm in diameter and 1.5 mm in length was inserted in the undrawn end portion, and then, its open end was heat-sealed, to thereby form an oval spherical tip part 0.8 mm in diameter and 2.5 mm in length. Thereafter, a tungsten wire having a tapered end portion and having a diameter of 0.25 mm and a length of 1.25 m was inserted in the other undrawn portion from the open end thereof, so that the tapered tip of the tungsten wire reached a midway point of the tapering part, and then, the open end was heat-sealed, whereby a monofilament guide wire was obtained.

The guide wire was used for a clinical examination wherein a catheter was advanced through the abdominal aorta into the left renal artery. The guide wire could be easily manipulated for the tip to reach the intended parts. The insertion of a catheter was also easy because of the lubricating property of the guide wire. The guide wire, withdrawn from the blood vessel, could be easily cleaned by lightly wiping it and had little or no thrombus deposition thereon.

EXAMPLE 4

A hollow polyethylene terephthalate monofilament having a diameter of 0.8 mm and a hollow diameter of 0.33 mm was prepared in a manner similar to that mentioned in Example 2. The continuous monofilament was cut into lengths of 1.3 m. One portion of each monofilament, which portion was adjacent to one end portion of the monofilament, was drawn about three times its original length, to thereby simultaneously form a flexible part 0.3 mm in diameter and 50 mm in length and a tapering part 30 mm in length. Then, a tungsten piece 0.3 mm diameter and 1.5 mm in length was inserted in the undrawn end portion, and then, its open end was heat-sealed, to thereby form an oval spherical tip part 0.8 mm in diameter and 2.5 mm in length. Thereafter, a tungsten wire having a tapered end portion and having a diameter of 0.25 mm and a length of 1.25 m was inserted into each monifilament from the end thereof opposite to the tip part, so that the tapered tip of the tungsten wire was directed toward the tip part and reached a midway point in the tapering part, and then, the open end was heat-sealed, to thereby obtain monofilament guide wires.

One portion of the guide wires was subjected to the following surface treatment (1).

(1) Silicone coating treatment

A 2 weight % solution of "MDX4-4159" (trade name, room temperature drying type silicone lubricant, supplied by Dow Corning Co.) in isopropanol was prepared. The guide wire was immersed in the silicone solution. After being withdrawn from the silicone solution the guide wire was wiped by a gauge to remove the excessive amount of the silicone solution, and then, dried under reduced pressure. The so treated guide wire is referred to as "guide wire A" for brevity.

The remaining portion of the guide wires was subjected to the following surface treatment (2).

(2) Fluorine-containing resin coating treatment

The guide wire was immersed in "Teflon 30 J" (trade name, an aqueous suspension containing 60 weight % of polytetrafluoroethylene having a particle size of about 0.3 micron, supplied by Mitsu Fluorochemical Co.). After being withdrawn from the suspension, the guide wire was dried under reduced pressure. The so treated guide wire is referred to as "guiding wire B" for brevity.

The guide wires A and B were used in a clinical examination, wherein a catheter was advanced through the abdominal aorta into the left renal artery. Both guide wires A and B could be easily manipulated for their tips to reach the intended parts. The insertion of the catheter and the withdrawal of the guide wire were also very easy. These guide wires, withdrawn from the blood vessel, could be easily cleaned by lightly wiping them and had little or no thrombus deposition thereon.

EXAMPLE 5

A hollow monofilament having a diameter of 0.8 mm and a hollow diameter of 0.33 mm was prepared in a manner similar to that mentioned in Example 2, from a tetrafluoroethylene/hexafluoropropylene copolymer "Teflon" FEP resin (supplied by Mitsu Fluorochemical Co.). The continuous monofilament was cut into lengths of 1.3 m. One portion of each monofilament, which portion was adjacent to one end portion of the monofilament, was drawn about three times its original length, to thereby simultaneously form a flexible part 0.3 mm in diameter and 25 mm in length and a tapering part 30 mm in length. Then, a tungsten piece 0.3 mm in diameter and 1.5 mm in length was inserted in the undrawn end portion, and then, its open end was heat-sealed, to thereby form an oval, spherical tip part 0.8 mm in diameter and 2.5 mm in length. Thereafter, a tungsten wire having a tapered end portion and having a diameter of 0.25 mm and a length of 1.25 m was inserted into the monofilament from the end thereof opposite to the tip part, so that the tapered tip of the tungsten wire was directed toward the tip part and reached a midway point in the tapering part, and then, the open end was heat-sealed, to thereby obtain a monofilament guide wire.

The guide wire was used in a clinical examination, wherein a catheter was advanced through the abdominal aorta into the left renal artery. The guide wire could be easily manipulated for its tip to reach the intended parts. The insertion of the catheter and the withdrawal of the guide wire were also very easy. The guide wire withdrawn from the blood vessel had only a very slight amount of thrombus deposition therein.

EXAMPLE 6

Polyethylene terephthalate was melt-extruded in a conventional manner by using an extruder provided with a spinneret having a special orifice, to thereby obtain a multi-hollow monofilament having an overall diameter of 1 mm and having two continuously extending hollows, each 0.33 mm in diameter. The multi-hollow monofilament was cut into lengths of 1.5 m. One portion of each monofilament, which portion was adjacent to one end portion (about 1 mm in length) of the monofilament, was drawn about three times its original length, to thereby simultaneously form a flexible part 0.3 mm in diameter and 50 mm in length and a tapering part 30 mm in length. Then, two tungsten pieces, each 0.3 mm in diameter and 0.5 mm in length, were inserted into the two hollows, respectively, in the undrawn end portion of about 1 mm in length, and then, the open ends were heat-sealed. Thereafter, a tungsten wire having a tapered end portion and having a diameter of 0.25 mm was inserted into one of the two hollows extending form the end of the manipulating part to the end of the tapering part, so that the tapered tip of the tungsten wire was directed to the tip part and reached a point in close proximity to the end of the tapering part, and then, the open end of the hollow in which the tungsten wire was inserted was heat-sealed. A small opening having a diameter of 0.25 mm was drilled in the wall of the tapering part of the other hollow, to thereby form a medicament outlet opening through which the other hollow was opened into the outside.

The so obtained self-guiding type catheter, having a structure similar to that illustrated in FIGS. 7A and 7B, was used in a clinical examination, wherein the catheter was advanced from the abdominal aorta through the coeliac artery into the hepatic artery. Both images of the tip part and the manipulating part were very clear and could be easily monitored. The catheter could be easily manipulated for the tip of the catheter to reach the affected parts, for example, in a liver. The catheterization caused no adverse reaction to the patient. An exactly determined amount of a drug could be selectively administered to the affected parts by using a precision metering pump connected to the inlet opening of the catheter. This medical treatment required only a period of time equal to approximately ⅓ of the time required for the conventional procedure wherein a guide wire and a catheter are used. The catheter could be smoothly withdrawn from the blood vessel. The withdrawn catheter could be easily cleaned by wiping it with gauze, and had little or no thrombus deposition thereon.

What we claim is:

1. A medical vascular guide insertable into a blood vessel for travel along the interior thereof; comprising
   (a) an elongated tubular outer member having
      (i) a manipulating part of first cross-sectional area;
      (ii) a flexible part, of reduced cross-sectional area relative to said manipulating part;
      (iii) a tapering part, connecting said manipulating part and said flexible part;
   (b) an elongated metal member occupying the interior of said manipulating part of said tubular member;
   (c) a tip member at an end of said flexible part remote from said tapering part, of integral unitary construction with said tubular member, of enlarged cross-sectional area relative to said flexible part;
   (d) a second metal member occupying the interior of said tip portion;
   (e) wherein said manipulating, tapering and flexible parts and said tip member are integrally formed of a single synthetic resin monofilament.

2. A medical vascular guide according to claim 1, wherein said elongated metal member has an end portion which is tapered and extends from said manipulating part into said tapered part, such that said tapered end of said metal member is directed toward said tip part of said guide.

3. A medical vascular guide according to claim 1 or 2, wherein the monofilament is made of at least one melt-extrudable thermoplastic synthetic resin selected from the group consisting of polyesters, polyamides and polyolefins.

4. A medical vascular guide according to claim 1 or 2, wherein the monofilament is made of a polyblend comprised of, based on the total weight of the polyblend, (i) 70 to 90% by weight of at least one melt-extrudable thermoplastic synthetic resin selected from the group consisting of polyesters, polyamides and polyolefins and (ii) 1 to 30% by weight of a fluorine-containing thermoplastic resin.

5. A medical vascular guide according to claim 1 or 2, wherein the exterior of said tubular member and said tip member has been treated by (i) a silicone coating treatment, (ii) a fluorine-containing resin coating treatment, or (iii) a plasma spark discharge treatment effected in an atmosphere of a gaseous organic fluorine-containing compound.

6. A medical vascular guide according to claim 1 or 2, wherein the monofilament is made of a melt-extrudable fluorine-containing thermoplastic resin.

7. A medical vascular guide according to claim 1 or 2, wherein the respective parts of said tip member and said tubular member have the dimensions:
   tip part: maximum diameter is about 0.5–3 and length is about 0.5–5 mm;
   relatively flexible part: diameter is about 0.1–0.5 mm and length is about 10–100 mm;
   tapered part: length is about 10–100 mm, and;
   manipulating part: diameter is about 0.5–3 mm and length is at least about 200 mm.

8. A medical vascular guide according to claim 1 or 2, wherein said elongated metal member is made of tungsten.

9. A medical vascular guide according to claim 1, wherein a passageway is provided within said outer member having inlet and outlet openings for flow therethrough of fluids, one of said openings being proximate the manipulating part end remote from said tapering part and the remaining opening being proximate said tapering part.

10. A self-guiding type catheter comprising:
    (a) an elongated tubular outer member having
       (i) a manipulating part of first cross-sectional area;
       (ii) a flexible part, of reduced cross-sectional area relative to said manipulating part;
       (iii) a tapering part, connecting said manipulating part and said flexible part;
    (b) an elongated x-ray impermeable member occupying an interior portion of said manipulating part of said tubular member;

(c) a tip member at an end of said flexible part remote from said tapering part, of integral unitary construction with said tubular member, of enlarged cross-sectional area relative to said flexible part;

(d) at least one X-ray impermeable member occupying an interior portion of said tip portion;

(e) wherein said manipulating, tapering and flexible parts and said tip member are integrally formed of a single synthetic resin monofilament; and (f) a passageway within said outer member, having inlet and outlet openings for flow therethrough of fluids, one of said openings being proximate the manipulating part end remote from said tapering part and the remaining opening being proximate said tapering part.

11. A catheter according to claim 10, wherein said X-ray impermeable member occupying the interior of said manipulating part is a metal wire, one end portion of which is tapered and inserted in said manipulating part in a manner such that the tapered end of the metal wire is directed toward said tip member.

12. A catheter according to claim 10 or 11, wherein said synthetic resin monofilament is made of at least one melt-extrudable thermoplastic synthetic resin selected from the group consisting of polyesters, polyamides and polyolefins.

13. A catheter according to claim 10 or 11, wherein said synthetic resin monofilament is a polyblend comprised of, based on the total weight of the polyblend, (i) 70 to 99% by weight of at least one melt-extrudable thermoplastic synthetic resin selected from the group consisting of polyesters, polyamides and polyolefins and (ii) 1 to 30% by weight of a fluorine-containing thermoplastic resin.

14. A catheter according to claim 10 or 11, wherein the catheter body has been surface-treated by (i) a silicone coating treatment, (ii) a fluorine-containing resin coating treatment, or (iii) a plasma spark discharge treatment effected in an atmosphere of a gaseous organic fluorine-containing compound.

15. A catheter according to claim 10 or 11 wherein said synthetic resin monofilament is made of a melt-extrudable fluorine-containing thermoplastic resin.

16. A catheter according to claim 10 or 11, wherein the respective parts of said catheter have the dimensions:

tip member: a maximum diameter is about 0.53 mm and length is about 0.5–5 mm;

flexible part: diameter is about 0.1–0.5 mm and length is about 10–100 mm;

tapered part: length is about 10–100 mm, and;

manipulating part: diameter is about 0.7–3 mm and length is at least about 200 mm.

* * * * *